United States Patent
Yang et al.

(10) Patent No.: US 8,172,906 B2
(45) Date of Patent: May 8, 2012

(54) ARTIFICIAL JOINT FIXATION MECHANISM

(75) Inventors: Rong-Sen Yang, Taipei (TW);
Chao-Chang A. Chen, Taipei (TW);
Chen-Yu Lung, Taoyuan (TW);
Cheng-Kuang Lu, Keelung (TW)

(73) Assignee: United Orthopedic Corporation, Hsinchu (TW)

( * ) Notice: Subject to any disclaimer, the term of this patent is extended or adjusted under 35 U.S.C. 154(b) by 0 days.

(21) Appl. No.: 11/404,087

(22) Filed: Apr. 14, 2006

(65) Prior Publication Data

US 2007/0244567 A1  Oct. 18, 2007

(51) Int. Cl.
*A61F 2/30* (2006.01)

(52) U.S. Cl. ............ 623/23.46; 623/22.45; 623/23.18; 623/23.44

(58) Field of Classification Search .......... 623/20.34, 623/20.36, 22.4, 22.42, 22.45, 23.15, 23.18, 623/23.21, 23.23, 23.44, 22.41, 23.22, 23.46, 623/20.15; 403/2, 7, 8, 48, 182, 183, 184, 403/202, 204, 217, 296, 299
See application file for complete search history.

(56) References Cited

U.S. PATENT DOCUMENTS

| 5,152,796 | A | * | 10/1992 | Slamin ........................ 623/20.15 |
| 5,683,472 | A | * | 11/1997 | O'Neil et al. .............. 623/20.31 |
| 6,090,146 | A | * | 7/2000 | Rozow et al. ............. 623/22.42 |
| 6,610,099 | B1 | * | 8/2003 | Albrektsson et al. ...... 623/23.15 |
| 6,692,530 | B2 | * | 2/2004 | Doubler et al. ........... 623/22.42 |
| 6,695,883 | B2 | * | 2/2004 | Crofford .................... 623/22.46 |
| 6,981,991 | B2 | * | 1/2006 | Ferree ........................ 623/23.46 |
| 7,105,029 | B2 | * | 9/2006 | Doubler et al. ........... 623/22.42 |

FOREIGN PATENT DOCUMENTS

JP  2001141158 A * 5/2001

* cited by examiner

*Primary Examiner* — David H Willse
*Assistant Examiner* — Javier Blanco
(74) *Attorney, Agent, or Firm* — Muncy, Geissler, Olds & Lowe, PLLC

(57) ABSTRACT

An artificial joint fixation mechanism has a base for being attached to an artificial joint, a stem for guiding an artificial joint to engage with a human bone, and a sleeve. The base defines a conic shaft hole therethrough. At least a positioning section and at least a threaded section are extended adjacent an end of the shaft hole. The stem includes an engaging pole at an end thereof for jointing to an artificial joint. The sleeve is threaded for screwing to the threaded section and defines an inner cone hole therethrough. In use, the engaging pole of the stem implants into the shaft hole. The sleeve is screwed to the threaded section, and the inner cone hole reversely pressing against the guiding section. Thus the stem is pressed reliably.

3 Claims, 5 Drawing Sheets

ARTIFICIAL JOINT FIXATION MECHANISM

BACKGROUND OF THE INVENTION (a) Field of the Invention

The present invention relates to an artificial joint fixation mechanism, and particularly to an artificial joint fixation mechanism which allows a stem movable in predetermined direction and provides bidirectional conic pressure for fixing an artificial joint.

(b) Description of the Prior Art

Artificial joints are often intended to replace human hip joints or knee joints, which are located on opposite sides of pelvis and bear most weight of a human. In the event that an artificial joint is placed or positioned improperly, jointing points thereof may disengage, and therefore the artificial joint can't firmly articulate with respect to a bone stem.

Moreover, as for diverse patents, flexion angles of bones are not identical. Artificial joints are precise so that need be engaged with bone stems at predetermined angles for preventing against disengagement resulting from inappropriate side force.

SUMMARY OF THE INVENTION

Accordingly, an object of the present invention is to provide an artificial joint fixation mechanism which facilitates an artificial joint engaging with a bone stem rapidly and precisely and prevents displacement of the artificial joint.

Another object of the present invention is to provide an artificial joint fixation mechanism which provides bidirectional conic pressure for fixing an artificial joint.

A further object of the present invention is to provide an artificial joint fixation mechanism which assures bending orientation of a bone stem.

An artificial joint fixation mechanism comprises a base attached to an artificial joint, a stem guiding an artificial joint to engage with a human bone, and a sleeve. The base is substantially cylindrical and defines a conic shaft hole therethrough. At least a positioning section and at least a threaded section are extended adjacent an end of the shaft hole. The stem includes an engaging pole at an end thereof for jointing to an artificial joint, a conic guiding section extending from the engaging pole, and at least a contact surface at an outer peripheral thereof. The sleeve is threaded for screwing to the threaded section and defines an inner cone hole therethrough. At least a notch is defined proximate an end of the inner cone hole. The engaging pole of the stem implants into the shaft hole. The contact surface of the stem fits with the positioning section. The sleeve is put to enclose the guiding section, driving the sleeve and the threaded section screw to each other, and the inner cone hole reversely pressing down the guiding section. Thus the stem is pressed by bidirectional cone jointing pressure.

The inner cone hole has cone angle corresponding to cone angle of the guiding section, whereby the stem forms an optimal implanting orientation relative to a human bone.

DETAILED DESCRIPTION OF THE PREFERRED EMBODIMENTS

Figures 1, 2:
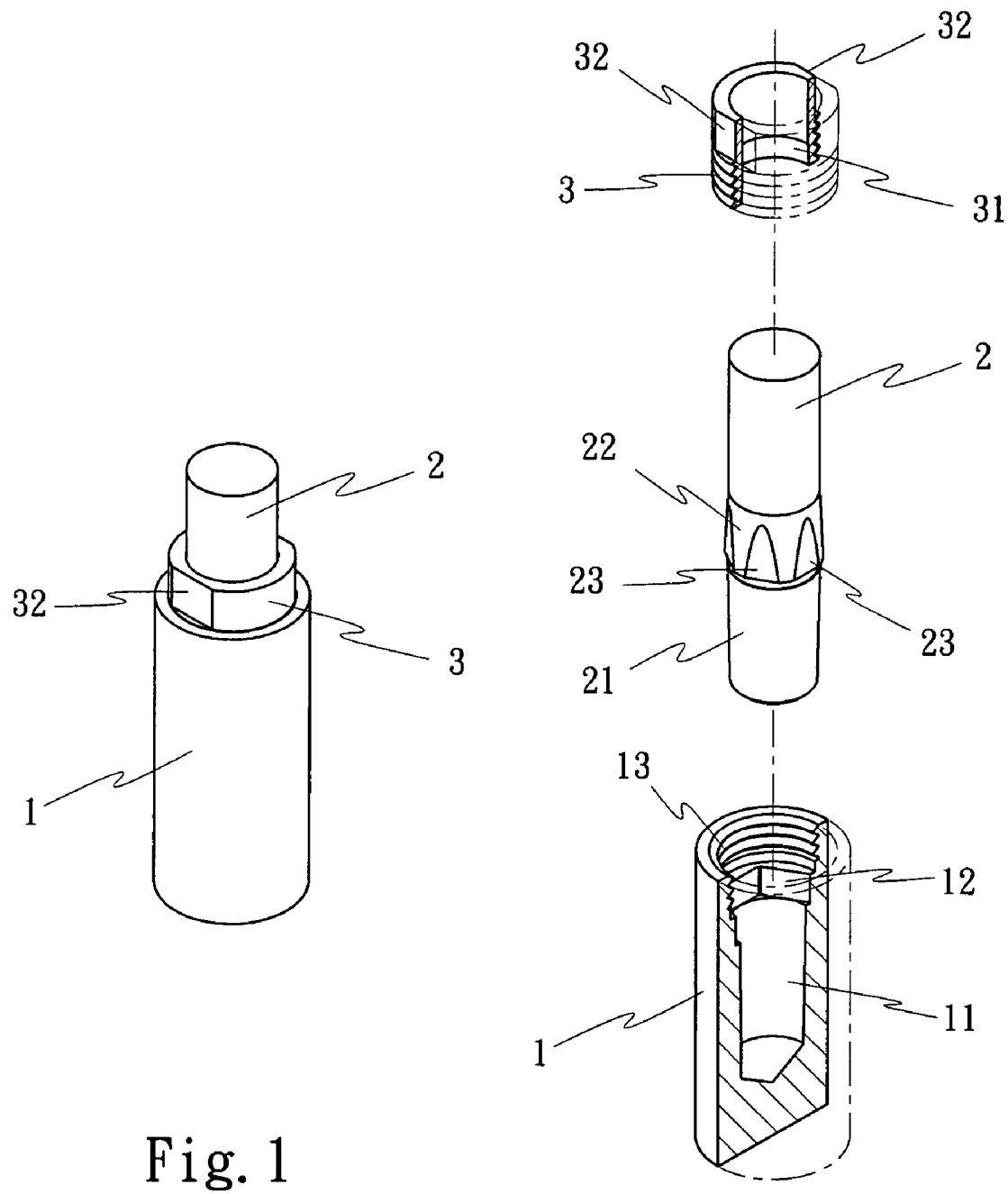
FIG. 1 is a perspective view of an artificial joint fixation mechanism according to the present invention.
FIG. 2 is an exploded view of the artificial joint fixation mechanism of FIG. 1.

With reference to FIGS. 1 and 2, an artificial joint fixation mechanism of the present invention comprises a base 1 attached to or unitarily formed on an artificial joint, a stem 2 and a sleeve 3.

Figure 4:
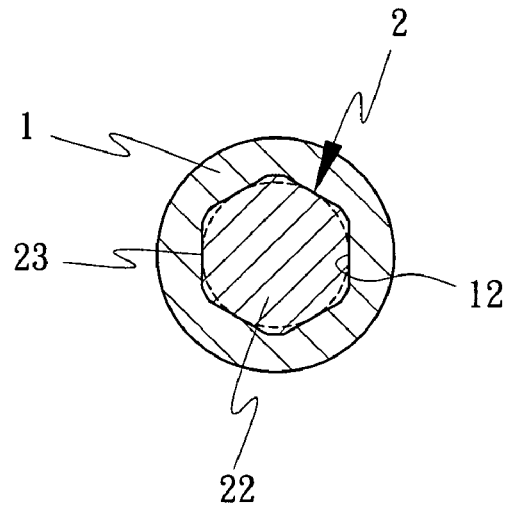
FIG. 4 is a cross-sectional view taken along the line A-A of FIG. 3 for clearly showing engagement of an engaging pole and a base.
Figure 5:
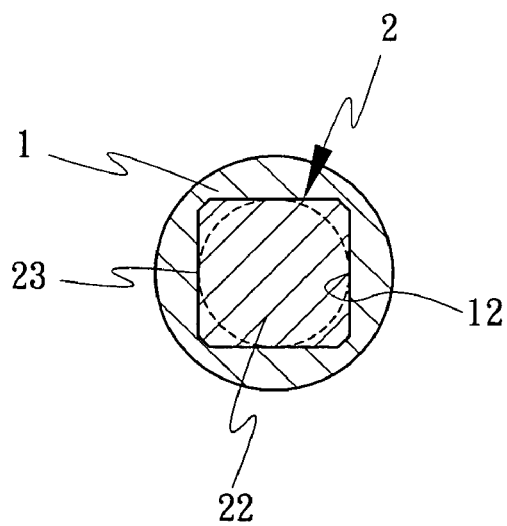
FIG. 5 is another cross-sectional view taken along the line A-A of FIG. 3 for clearly showing another engagement of an engaging pole and a base.

The base 1 is substantially cylindrical and defines a conic shaft hole 11 through a center thereof. At least a positioning section 12 and at least a threaded section 13 are extended in sequence adjacent an end of the shaft hole 11. The positioning section 12 may be bordered as any desired polygon shape, for example, a hexagon in FIG. 4 or a quadrangle in FIG. 5.

The stem 2 is used to guide an artificial joint to engage with a human bone. The stem 2 includes a conic engaging pole 21 at an end thereof for jointing to an artificial joint, a conic guiding section 22 extending from an end of the engaging pole 21, and at least a contact surface 23 at an outer peripheral of the guiding section 22. The contact surface 23 may be distributed as any desired polygon shape, for example, a hexagon in FIG. 4 or a quadrangle in FIG. 5.

The sleeve 3 is threaded for screwing to the threaded section 13, and defines an inner cone hole 31 through a center thereof. At least a notch 32 is defined in an outer rim of an end of the inner cone hole 31. The inner cone hole 31 has cone angle corresponding to cone angle of the guiding section 22.

Figure 3:
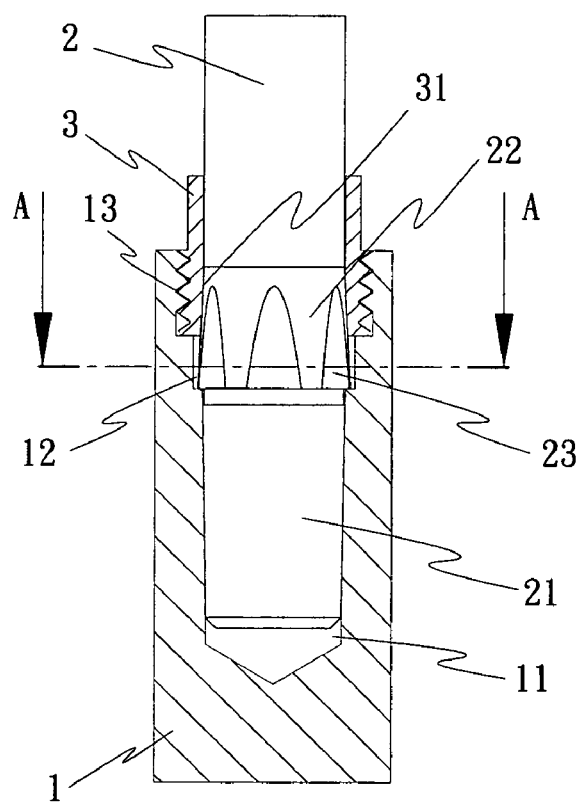
FIG. 3 is a cross-sectional view taken along a longitudinal middle of the artificial joint fixation mechanism of FIG. 1.

Referring to FIG. 3, the engaging pole 21 of the stem 2 implants into the shaft hole 11 of the base 1. The shaft hole 11 has cone angle corresponding to cone angle of the engaging pole 21. The contact surface 23 of the stem 2 fits with the positioning section 12 of the base 1. The sleeve 3 is put to enclose the guiding section 22 of the stem 2. The sleeve 3 and the threaded section 13 screw to each other, the inner cone hole 31 reversely pressing against the guiding section 22. Thus the stem 2 is pressed by bidirectional cone jointing pressure, and is retainedly fixed and positioned.

Figure 6:
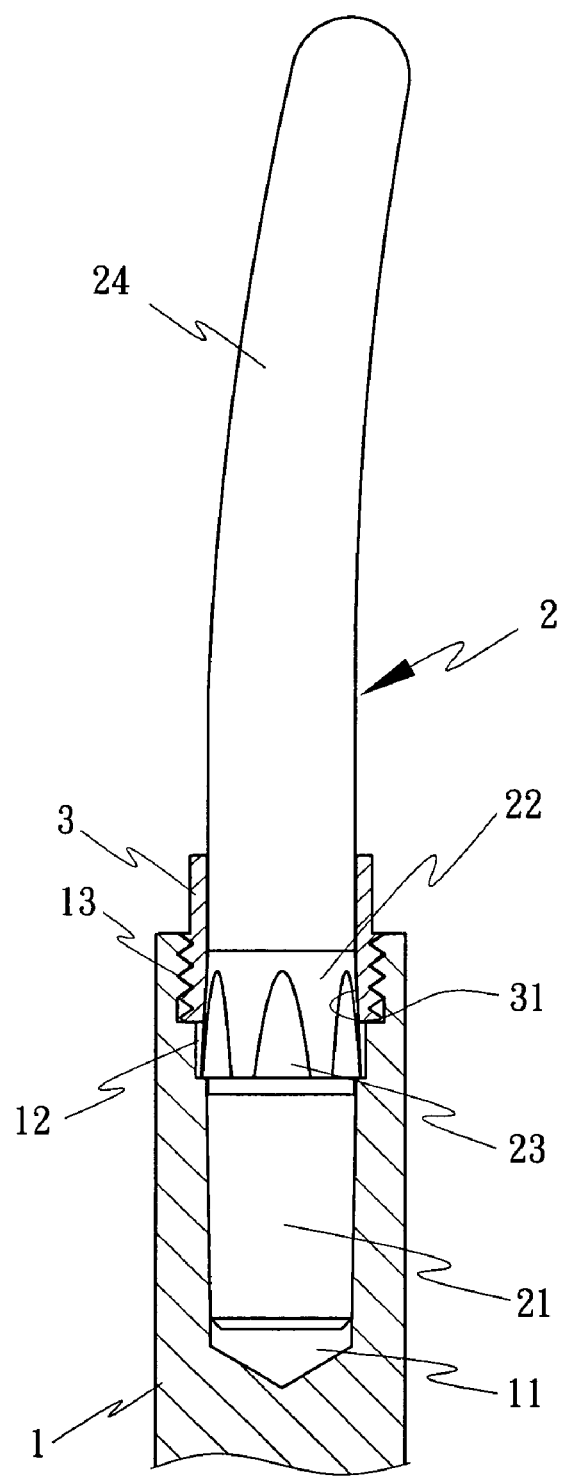
FIG. 6 is similar to FIG. 3, further showing a body portion of a stem.

Engagement between the guiding section 12 and the contact surface 23 limits the stem 2 movable in a single predetermined direction. In detail, the stem 2 is fixed to the base 1 by the sleeve 3, and a body portion 24 of the stem 2, which extends from an end of the guiding section 22 and is exposed beyond the base 1, is positioned with a prescribed bending orientation, as shown in FIG. 6. The body portion 24 forms an optimal implanting orientation relative to a human bone only in the case that the stem 2 is irrotational. In fact, the stem 2 is not rotatable when the guiding section 12 and the contact surface 23 have corresponding fixable polygon shape, for example, a hexagon in FIG. 4 or a quadrangle in FIG. 5, as described above.

Figure 7:
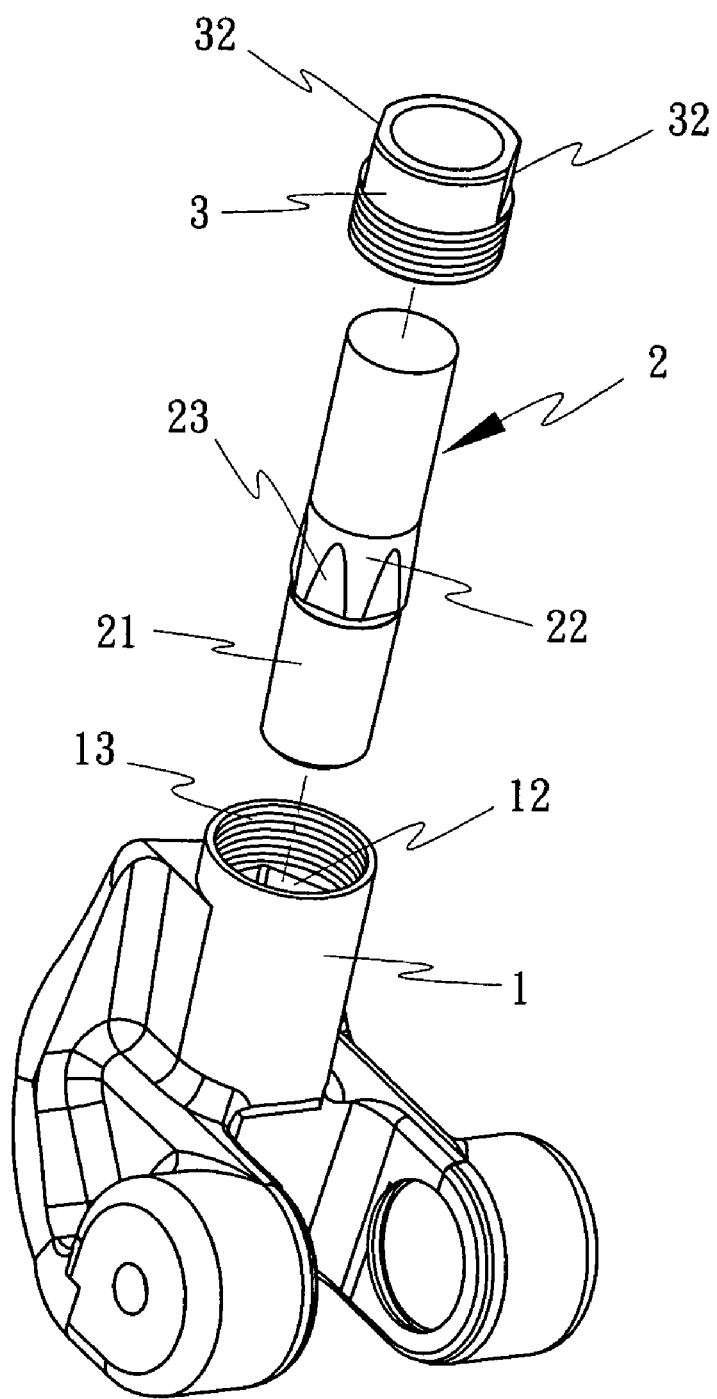
FIG. 7 is an exploded view of the artificial joint fixation mechanism applied on a knee joint.
Figure 8:
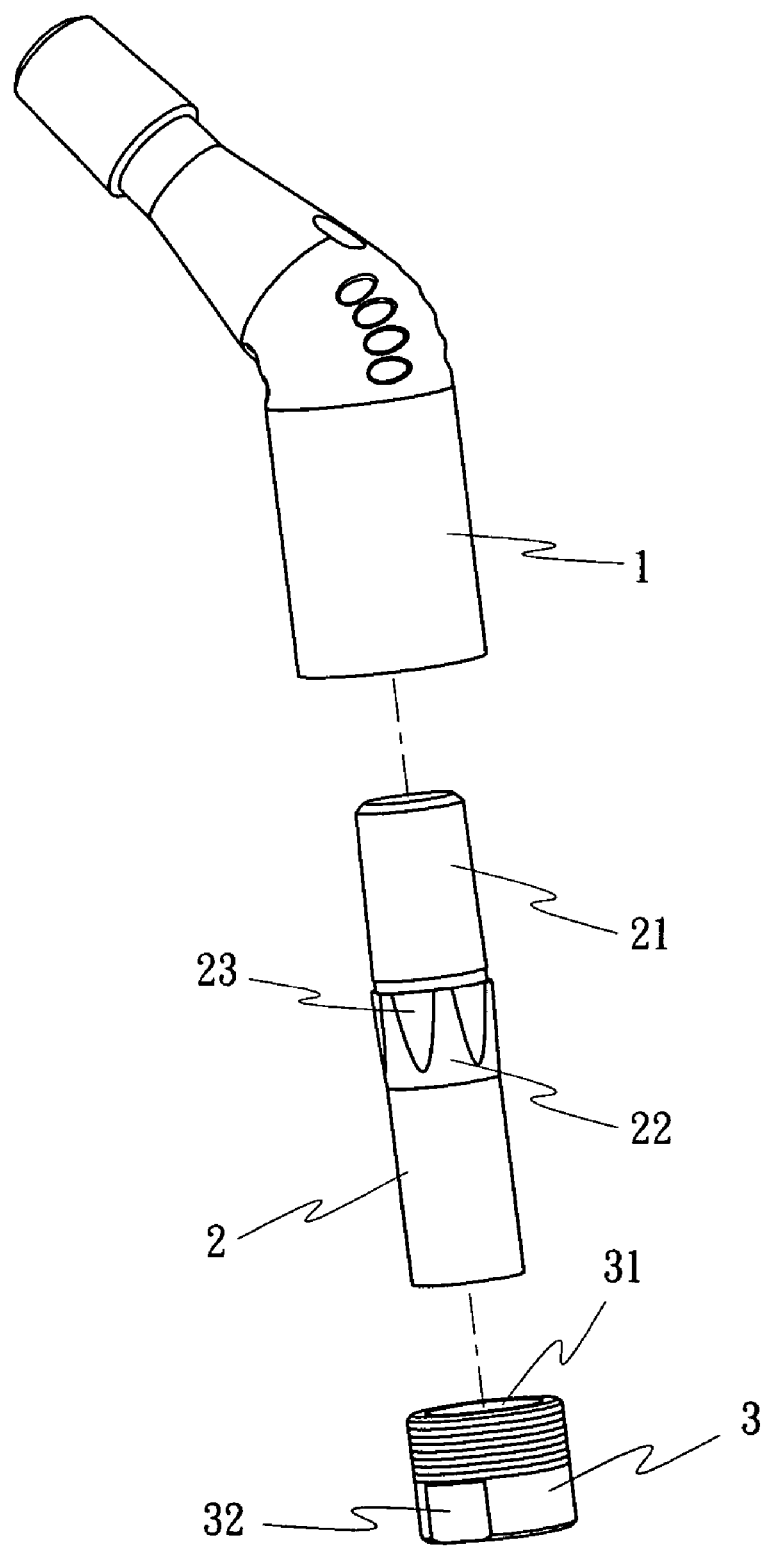
FIG. 8 is an exploded view of the artificial joint fixation mechanism applied on a hip joint.

The engaging pole 21 and the shaft hole 11 are fit to each other with cone shape, and the guiding section 22 and the inner cone hole 31 are also fit to each other with cone shape, exerting bidirectional cone pressure force to the stem 2, thereby effectively clamping and fixing the stem 2. The artificial joint fixation mechanism is practicably applied to artificial joints, for instance, a knee joint illustrated in FIG. 7 and a hip joint illustrated in FIG. 8. In these applications, the artificial joints reliably support weight of a human and prevent from displacement or disengagement.

It is understood that the invention may be embodied in other forms without departing from the spirit thereof. Thus, the present examples and embodiments are to be considered in all respects as illustrative and not restrictive, and the invention is not to be limited to the details given herein.

What is claimed is:

1. An artificial joint fixation mechanism for use with an artificial joint, the artificial joint fixation mechanism comprising:
   a) a substantially cylindrical base to be attached to the artificial joint and having:
      i) a conic shaft hole therethrough;
      ii) a positioning section located in the conic shaft hole; and
      iii) a threaded section located in the conic shaft hole between the positioning section and an end of the base, the threaded section being adjacent to the positioning section;
   b) a stem for guiding the artificial joint to engage with a human bone, said stem having:
      i) a conic engaging pole located on a first end of the stem and being inserted into the conic shaft hole of the base;
      ii) a conic guiding section, the positioning section of the base limiting a distance the conic engaging pole and the conic guiding section are inserted into the conic shaft hole;
      iii) a contact surface located on an exterior surface of the conic guiding section and having a shape corresponding to a shape of the positioning section of the base; and
      iv) a body portion located on a second end of the stem, the conic guiding section is located between the conic engaging pole and the body portion; and
   c) a sleeve threadedly connected to the threaded section of the base and having an inner cone hole therethrough, the body portion of the stem being inserted through the inner cone hole of the sleeve, the inner cone hole of the sleeve pressing the conic guiding section of the stem against the inner cone hole of the sleeve and securing the stem in a predetermined position relative to the base,
   wherein the positioning section has a cross section having a shape selected from a group consisting of a polygon, a hexagon, and a quadrangle,
   wherein the contact surface of the stem has a cross section having a shape selected from a group consisting of a polygon, a hexagon, and a quadrangle, and
   wherein the conic shaft hole of the base has a cone angle corresponding to a cone angle of the conic engaging pole of the stem.

2. The artificial joint fixation mechanism according to claim 1, wherein the inner cone hole of the sleeve has a cone angle corresponding to a cone angle of the conic guiding section of the stem.

3. The artificial joint fixation mechanism according to claim 1, wherein the sleeve includes at least one notch located on an exterior thereof.

* * * * *